(12) United States Patent
Andrews et al.

(10) Patent No.: US 6,929,652 B1
(45) Date of Patent: Aug. 16, 2005

(54) DELIVERY AND RECOVERY SYSTEMS HAVING STEERABILITY AND RAPID EXCHANGE OPERATING MODES FOR EMBOLIC PROTECTION SYSTEMS

(75) Inventors: Christopher C. Andrews, Murrieta, CA (US); William J. Boyle, Fallbrook, CA (US); Sergio Correa, Encinitas, CA (US); Andy E. Denison, Temecula, CA (US); Benjamin C. Huter, Murrieta, CA (US); Scott J. Huter, Temecula, CA (US); Brad Jordan, Wildomar, CA (US); Paul Muller, San Carlos, CA (US); Paul V. Neale, San Diego, CA (US); Samir Patel, Fremont, CA (US); Richard Stack, Chapel Hill, NC (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 625 days.

(21) Appl. No.: 09/872,692

(22) Filed: Jun. 1, 2001

(51) Int. Cl.[7] .............................................. A61M 29/00
(52) U.S. Cl. ...................... 606/200; 606/108; 606/191; 606/198
(58) Field of Search ................................ 606/200, 159, 606/1, 108, 191, 194, 198

(56) References Cited

U.S. PATENT DOCUMENTS

| 4,473,067 A | 9/1984 | Schiff |
| 4,747,833 A | 5/1988 | Kousai et al. |
| 5,848,964 A | 12/1998 | Samuels |
| 6,159,198 A | 12/2000 | Gardeski et al. |
| 6,171,327 B1 * | 1/2001 | Daniel et al. ................ 606/200 |
| 6,171,328 B1 | 1/2001 | Addis |
| 6,179,859 B1 | 1/2001 | Bates et al. |
| 6,458,099 B2 | 10/2002 | Dutta et al. |
| 6,537,294 B1 * | 3/2003 | Boyle et al. ................. 606/200 |
| 6,733,486 B1 | 5/2004 | Lee et al. |
| 2001/0029362 A1 * | 10/2001 | Sirhan et al. ................ 604/524 |
| 2002/0022858 A1 * | 2/2002 | Demond et al. ............. 606/200 |
| 2002/0035347 A1 * | 3/2002 | Bagaoisan et al. ............ 604/35 |
| 2002/0052626 A1 * | 5/2002 | Gilson et al. ................ 606/200 |
| 2002/0133217 A1 * | 9/2002 | Sirhan et al. ............... 623/1.11 |
| 2004/0054347 A1 * | 3/2004 | Zadno-Azizi et al. ........ 604/509 |

* cited by examiner

Primary Examiner—Kim M. Lewis
Assistant Examiner—Andrea M. Ragonese
(74) Attorney, Agent, or Firm—Fulwider Patton Lee & Utecht, LLP

(57) ABSTRACT

A system for enabling the insertion and removal of an embolic protection device, for capturing and retaining embolic debris which may be created during the performance of a therapeutic interventional procedure in a stenosed or occluded region of a blood vessel. The system, in an embodiment thereof, is capable of enabling at least one operator to control the delivery and removal of an embolic protection device to a position in a patient's vasculature distal to an interventional procedure site, to enable the exchange of the delivery and recovery system. The system, in another embodiment thereof, includes a delivery system and a recovery system which are capable of enabling the delivery and recovery of an embolic protection device so as to maintain a clinically acceptable profile and flexibility through the patient's vasculature.

25 Claims, 7 Drawing Sheets

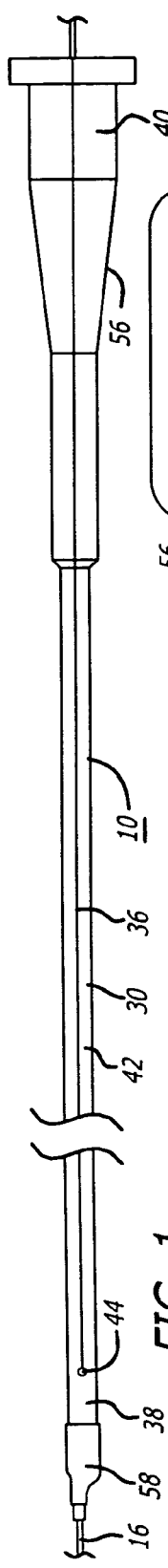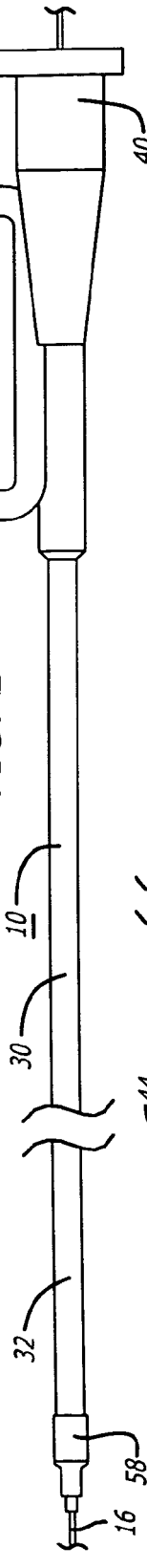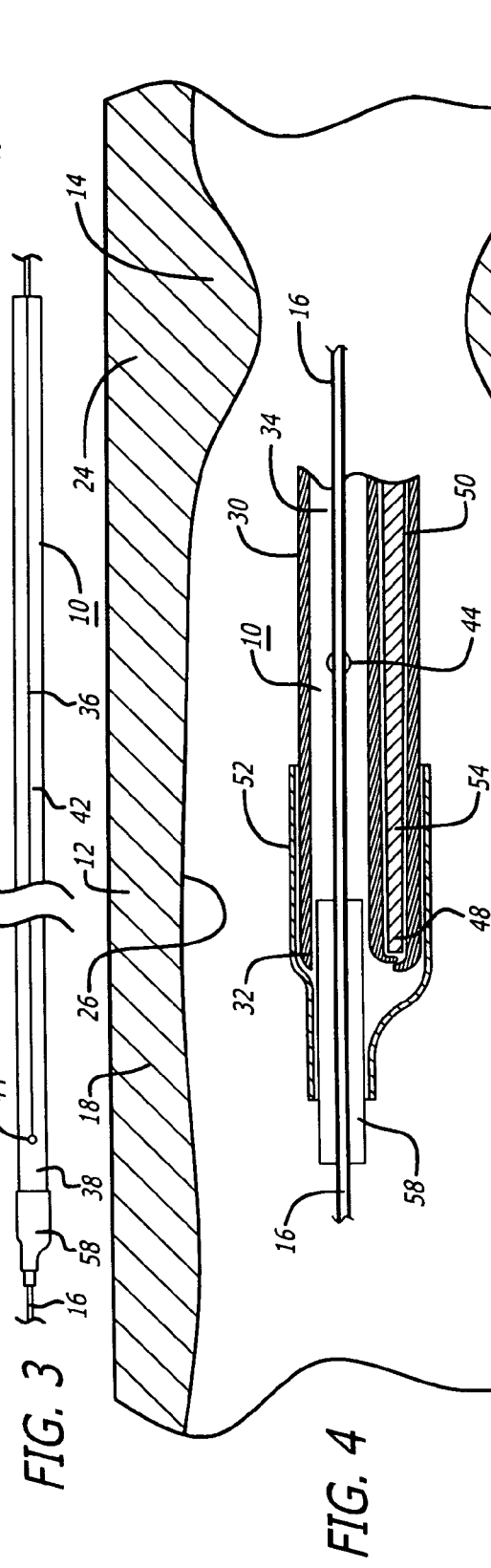

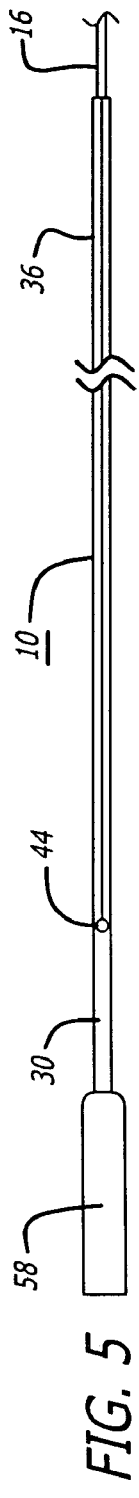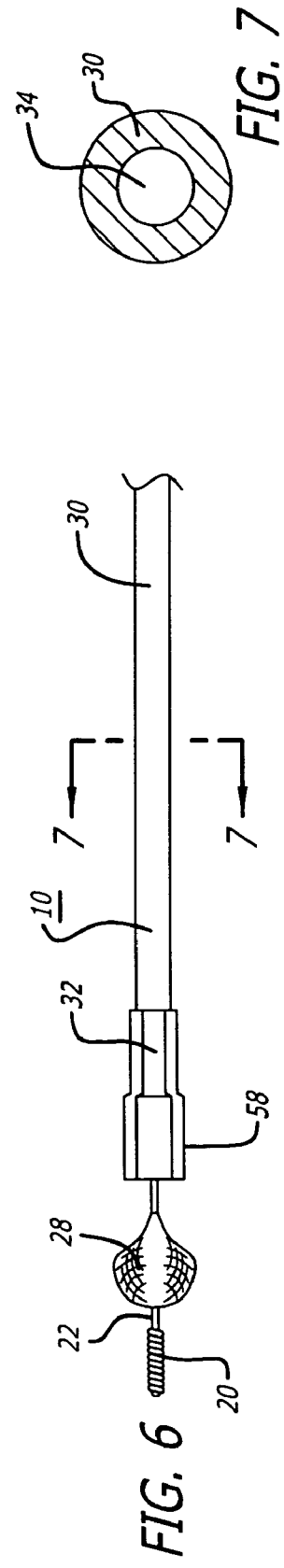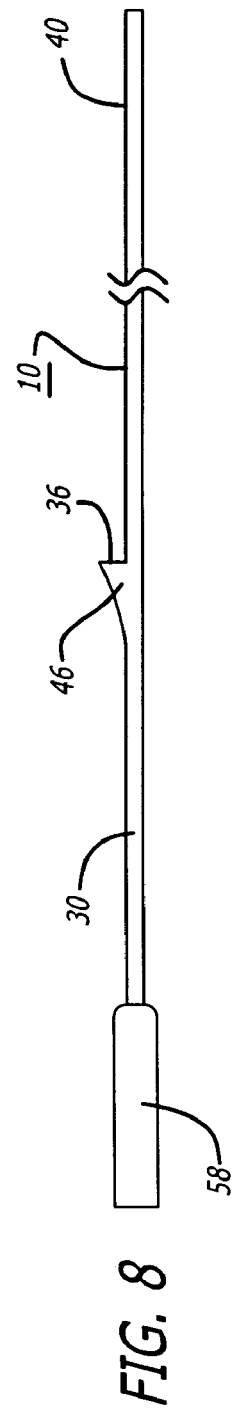

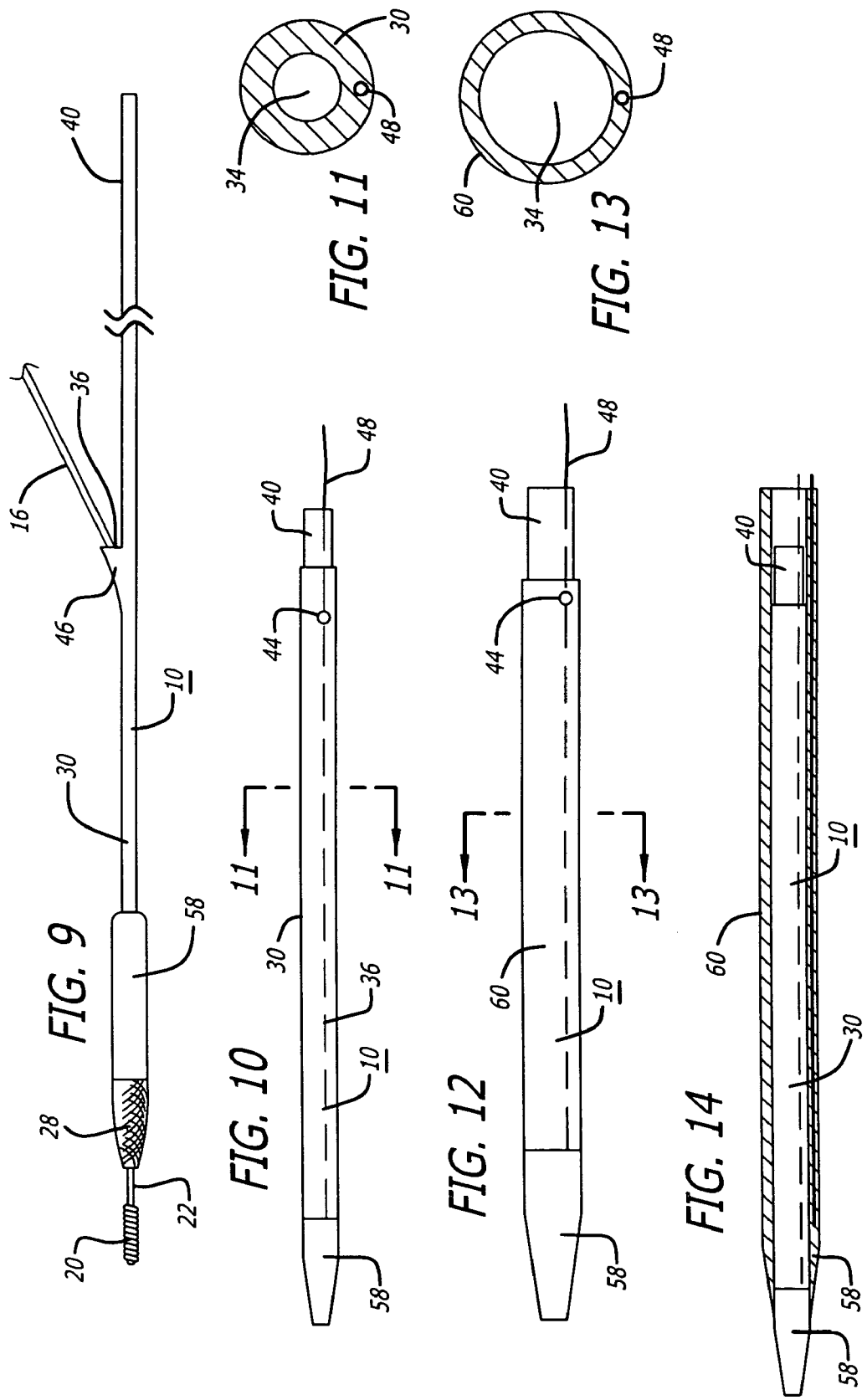

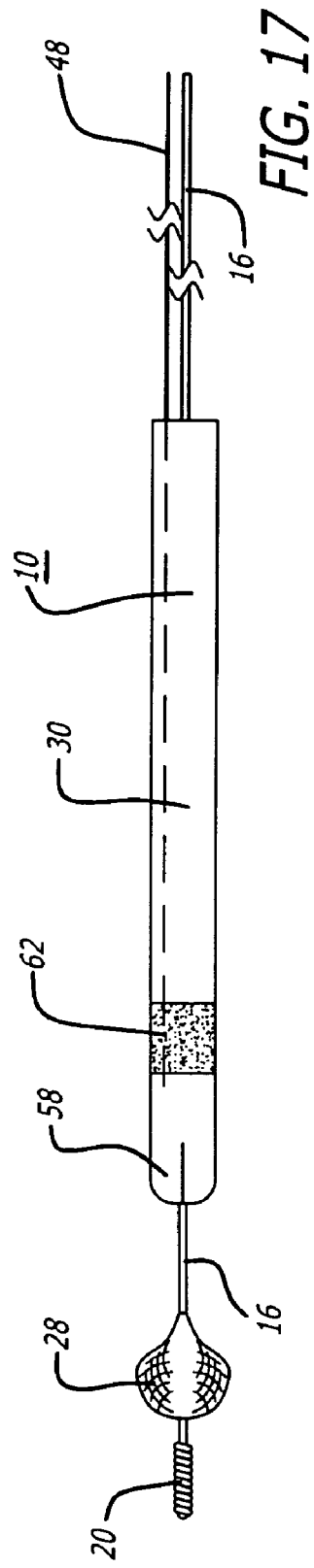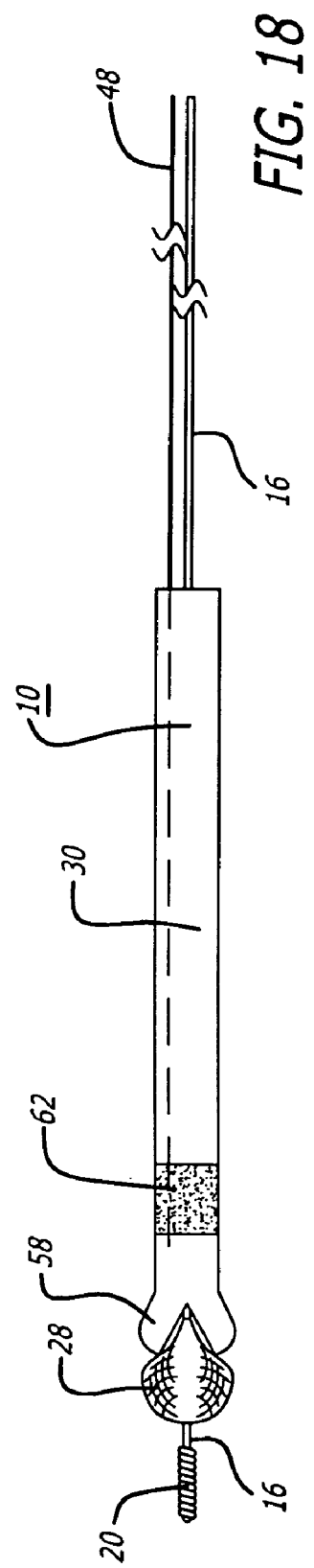

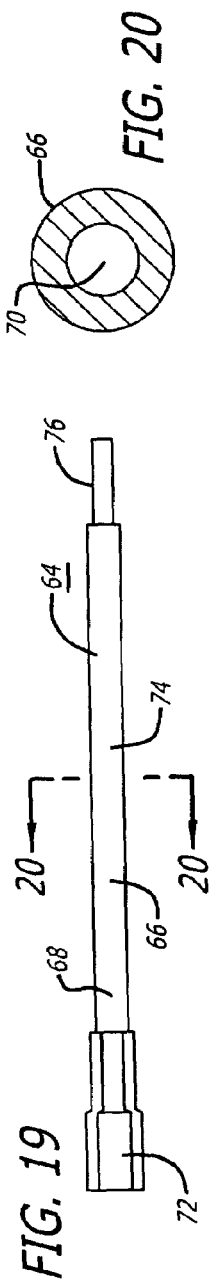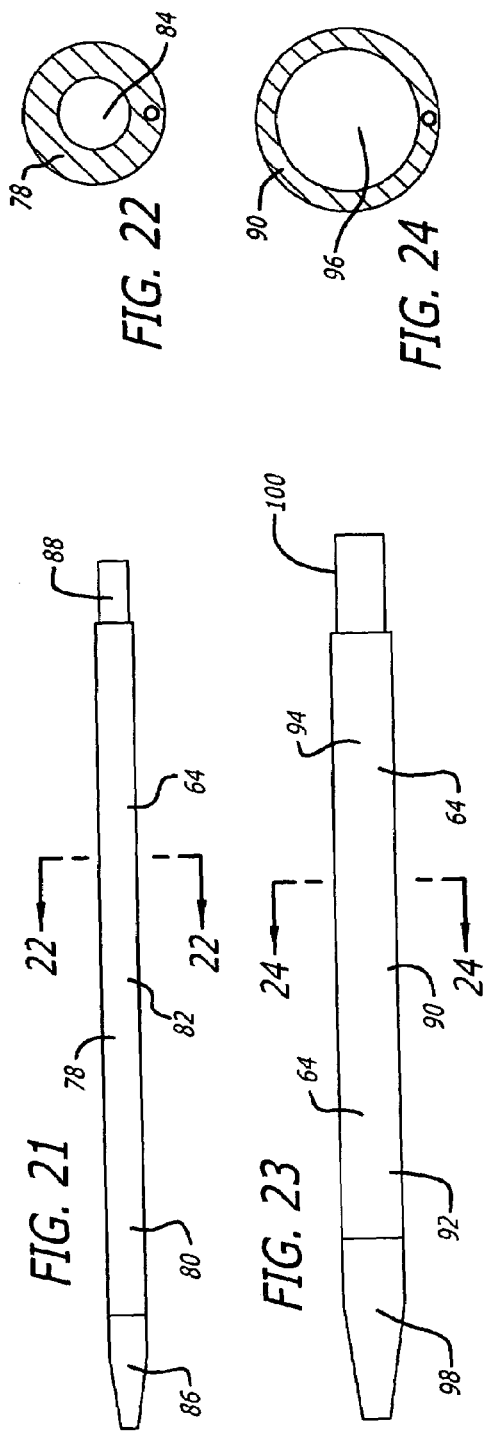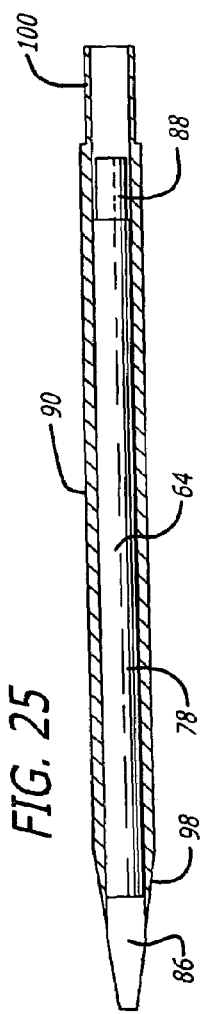

DELIVERY AND RECOVERY SYSTEMS HAVING STEERABILITY AND RAPID EXCHANGE OPERATING MODES FOR EMBOLIC PROTECTION SYSTEMS

BACKGROUND OF THE INVENTION

The present invention relates generally to improvements in embolic protection systems and methods. In particular, it relates to an improved system and method for enabling at least one operator to effectively deliver an embolic protection device to a position in a patient's vasculature distal to an interventional procedure site. The deployment of the embolic protection device is enabled so as to filter the blood in a blood vessel, to capture embolic material that may be created and released into the bloodstream during the performance of the interventional procedure in a stenosed or occluded region of a blood vessel. The invention also enables the operator to efficiently remove the embolic protection device from the interventional procedure site with the captured embolic material therein.

The present invention further particularly relates to an improved system and method for maintaining a clinically acceptable profile and flexibility during the delivery and removal of the embolic protection device through the patient's vasculature. The systems and methods of the present invention are particularly useful when performing balloon angioplasty, stenting procedures, laser angioplasty or atherectomy in critical vessels, such as the carotid, renal, and saphenous vein graft arteries, where the release of embolic debris into the bloodstream could possibly occlude the flow of oxygenated blood to the brain or other vital organs which can cause devastating consequences to the patient.

A variety of non-surgical interventional procedures have been developed over the years for opening stenosed or occluded blood vessels in a patient caused by the build up of plaque or other substances on the walls of the blood vessel. Such procedures usually involve the percutaneous introduction of the interventional device into the lumen of the artery, usually through a catheter. One widely known and medically accepted procedure is balloon angioplasty in which an inflatable balloon is introduced within the stenosed region of the blood vessel to dilate the occluded vessel. The balloon catheter is initially inserted into the patient's arterial system and is advanced and manipulated into the area of stenosis in the artery. The balloon is inflated to compress the plaque and press the vessel wall radially outward to increase the diameter of the blood vessel.

Another procedure is laser angioplasty which utilizes a laser to ablate the stenosis by super heating and vaporizing the deposited plaque. Atherectomy is yet another method of treating a stenosed blood vessel in which a cutting blade is rotated to shave the deposited plaque from the arterial wall. A vacuum catheter may be used to capture the shaved plaque or thrombus from the blood stream during this procedure.

In another widely practiced procedure, the stenosis can be treated by placing a device known as a stent into the stenosed region to hold open and sometimes expand the segment of the blood vessel or other arterial lumen. Stents are particularly useful in the treatment or repair of blood vessels after a stenosis has been compressed by percutaneous transluminal coronary angioplasty (PTCA), percutaneous transluminal angioplasty (PTA) or removal by atherectomy or other means. Stents are usually delivered in a compressed condition to the target site, and then are deployed at the target location into an expanded condition to support the vessel and help maintain it in an open position.

In the past, stents typically have fallen into two general categories of construction. The first type of stent is expandable upon application of a controlled force, often through the inflation of the balloon portion of a dilatation catheter which, upon inflation of the balloon or other expansion means, expands the compressed stent to a larger diameter to be left in place within the artery at the target site. The second type of stent is a self-expanding stent formed from, for example, shape memory metals or super-elastic nickel-titanium (NiTi) alloys, which will automatically expand from a compressed state when the stent is advanced out of the distal end of the delivery catheter into the body lumen. Such stents manufactured from self-expandable materials allow for phase transformations of the material to occur, contributing to the expansion and contraction of the stent.

The above non-surgical interventional procedures, when successful, avoid the necessity of major surgical operations. However, there is one common problem associated with all of these non-surgical procedures, namely, the potential release of embolic debris into the bloodstream which can occlude distal vasculature and cause significant health problems to the patient. For example, during deployment of a stent, it is possible that the metal struts of the stent can cut into the stenosis and shear off pieces of plaque which become embolic debris that can travel downstream and lodge somewhere in the patient's vascular system. Pieces of plaque material can sometimes dislodge from the stenosis during a balloon angioplasty procedure and become released into the bloodstream. Additionally, while complete vaporization of plaque is the intended goal during a laser angioplasty procedure, particles are not always fully vaporized and may enter the bloodstream.

When any of the above-described procedures are performed for example in the carotid arteries, the release of emboli into the circulatory system can be extremely dangerous to the patient. Debris that is carried by the bloodstream to distal vessels of the brain may cause these cerebral vessels to occlude, resulting in a stroke, and in some cases, death. Therefore, although carotid percutaneous transluminal angioplasty has been performed in the past, the number of procedures performed has been limited due to the justifiable fear of causing an embolic stroke should embolic debris enter the bloodstream and block vital downstream blood passages.

Medical devices have been developed to attempt to deal with the problem created when debris or fragments enter the circulatory system following treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such procedures in the carotid arteries a high-risk proposition.

Other techniques which have been developed to address the problem of removing embolic debris include the use of catheters with a vacuum source which provides temporary suction to remove embolic debris from the bloodstream. However, as mentioned above, there have been complications with such systems since the vacuum catheter may not always remove all of the embolic material from the bloodstream, and a powerful suction could cause problems to the patient's vasculature.

Further techniques which have had some limited success include the placement of an embolic protection device such as a filter or trap downstream from the treatment site to capture embolic debris before it reaches the smaller blood vessels downstream. Such embolic protection devices are adapted to enable the filtering of embolic debris which may be released into the bloodstream during the treatment to the vessel, and yet allow a sufficient amount of oxygenated blood to flow past the device to supply vital organs downstream from the treatment site.

However, there have been problems associated with embolic protection devices, particularly during the insertion, expansion, deployment, and removal of the embolic protection device within the blood vessel. The manipulation of the guide wire and the catheter employed in the insertion and removal of the embolic protection device usually requires two operators, one for manipulating the guide wire, and one for manipulating the catheter. This can sometimes prove to be a somewhat inefficient and inconvenient method for inserting and removing filtering systems. Also, a long guide wire was required previously for the delivery and removal of the embolic protection device, since the guide wire had to be held until the entire catheter was removed from the body, so that the guide wire could be grabbed as it exited the body and the catheter could be removed from the guide wire. Further, very substantial pullback force on the guide wire and catheter was required, due to the operation of frictional forces and the interaction thereof. Also, the insertion and removal of embolic protection devices through a patient's vasculature, if not properly implemented, subjected the patient's vasculature to potential trauma and would interfere with the treatment of the stenosis while increasing the likelihood of damage thereto.

Therefore, the present invention provides improved systems and methods for treating stenosis in blood vessels which enable at least one operator to manipulate the guide wire and the catheter, so as to efficiently and effectively deliver an embolic protection device to a position distal to an interventional procedure site for deployment thereof. The operator also can remove the embolic protection device with captured embolic material therein from the interventional procedure site. The improved systems and methods of the present invention further enable the treatment of a stenosis in blood vessels while maintaining a clinically acceptable profile and flexibility during the delivery and removal of the embolic protection device through the patient's vasculature. Moreover, the systems and methods are adapted to be relatively easy for a physician to use, while enabling the effective delivery and recovery of a filtering system capable of removing embolic debris released into the bloodstream. The inventions disclosed herein satisfy these and other needs.

SUMMARY OF THE INVENTION

The present invention, in general, provides a system and method for the insertion and removal of a filtering system for capturing and retaining embolic debris from a blood vessel. The embolic debris may be created during the performance of a therapeutic interventional procedure, such as a balloon angioplasty or stenting procedure. The filtering system is adapted to prevent the embolic debris from lodging and blocking blood vessels downstream from the interventional site. The present invention is particularly useful for enabling an interventional procedure to be performed in vital arteries, such as the carotid arteries, in which critical downstream blood vessels can become blocked with embolic debris, including the main blood vessels leading to the brain or other vital organs. As a result, the present invention provides the physician with a higher degree of confidence in the efficient delivery and recovery of a filtering system for the collection and removal of embolic debris from the blood vessel when performing high-risk interventional procedures.

The present invention enables a filtering system to be deployed in the blood vessel at a location distal to the area of treatment in the interventional procedure site. It also enables the blood to pass therethrough to enable blood to flow past the filter. It further enables the blood to be filtered to capture and retain any embolic debris which may be created during the interventional procedure.

More particularly, for example, in an embodiment of the present invention, a system is adapted to enable at least one operator to control the delivery of an embolic protection device to a position in a patient's vasculature distal to an interventional procedure site, for deployment of the embolic protection device. The present invention also enables the operator to control the removal of the delivery system from the patient's vasculature, to enable the exchange of the delivery and recovery system. It further enables the operator to control the position of a deployed embolic protection device within the patient's vasculature during an exchange of interventional devices.

The delivery system includes a guide wire, having a distal end, and adapted to be positioned within the blood vessel and to extend to a position distal to the interventional procedure site. The guide wire is further adapted to include an embolic protection device mounted on the distal end thereof. The system also includes a catheter, having a distal end, wherein the catheter has a lumen therein extending in the catheter to the distal end thereof. The guide wire and the embolic protection device are adapted to extend in and through the lumen in the catheter. The catheter and the guide wire are adapted to enable the embolic protection device to be delivered and deployed distal to the interventional procedure site. The catheter includes a manipulation-enabling element for enabling the operator to manipulate the guide wire and the catheter independently so as to enable removal thereof from the patient's vasculature.

The system in such embodiment further includes a system for enabling the at least one operator to control the recovery of the embolic protection device, from the delivered and deployed position thereof, for the exchange of the recovery system. The recovery system includes the catheter, including the manipulation-enabling element, for enabling the operator to independently manipulate the guide wire and the catheter, so as to enable removal of the catheter and the embolic protection device recovered thereby from the patient's vasculature.

In another embodiment of the present invention, for example, a delivery system is adapted to enable the delivery of an embolic protection device to a position in a patient's vasculature distal to an interventional procedure site, through the patient's vasculature, for deployment of the embolic protection device. The delivery system is adapted to maintain a clinically acceptable profile and flexibility during the delivery and removal thereof through the patient's vasculature.

The delivery system includes a guide wire, including a distal end, adapted to be positioned within the blood vessel and to extend to a position distal to the interventional procedure site, and to include an embolic protection device mounted on the distal end thereof. The delivery system further includes a delivery sheath, including a distal end, and a lumen therein extending in the delivery sheath to the distal end thereof, and wherein the guide wire and the embolic protection device are adapted to extend in and through the lumen. The delivery sheath and the guide wire are adapted to enable the embolic protection device to be delivered and deployed distal to the interventional procedure site. The delivery sheath comprises dimensions and materials adapted to provide a low profile, flexibility for enabling tracking thereof through the patient's vasculature, and rigidity for enabling pushing thereof through the patient's vasculature, so as to maintain a clinically acceptable profile and flexibility during the delivery and removal thereof through the patient's vasculature.

The system in such other embodiment also includes a recovery system, adapted to enable the recovery of the embolic protection device from the position in the patient's vasculature distal to the interventional procedure site, for removal of the embolic protection device. The recovery system is adapted to maintain a clinically acceptable profile and flexibility during the delivery and removal of the recovery system through the patient's vasculature.

The recovery system includes an inner catheter, including a distal end. The inner catheter has a lumen therein extending in the inner catheter to the distal end thereof, and wherein the inner catheter is adapted to extend over the guide wire, and the distal end of the inner catheter is adapted to be positionable adjacent the embolic protection device. The inner catheter comprises dimensions and materials adapted to enable a smooth transition for movement thereof along the guide wire, to inhibit kinking of the guide wire during the delivery and removal of the inner catheter, and to maintain a clinically acceptable profile and flexibility during the delivery and removal thereof through the patient's vasculature.

The recovery system further includes an outer catheter, including a distal end, wherein the outer catheter has a lumen therein extending in the outer catheter to the distal end thereof. The outer catheter is adapted to extend over the inner catheter. The outer catheter comprises dimensions and materials adapted to enable a smooth transition for movement thereof along the inner catheter, to enable the capturing of the embolic protection device, and to inhibit trauma to the patient's vasculature, so as to maintain a clinically acceptable profile and flexibility during the delivery and removal thereof through the patient's vasculature.

The above objects and advantages of the present invention, as well as others, are described in greater detail in the following description, when taken in conjunction with the accompanying drawings of illustrative embodiments.

BRIEF DESCRIPTION OF THE DRAWINGS

FIG. 1 is a side elevational partly broken view of a first form of a delivery version of a first embodiment of the present invention, including a guide wire and a delivery catheter.

FIG. 2 is a top plan view of the first form of a delivery version of the first embodiment shown in FIG. 1.

FIG. 3 is a similar view of the first form of the delivery version of the first embodiment shown in FIG. 1, without a handle at the proximal end of the delivery catheter.

FIG. 4 is an elevational fragmentary partly-sectional view of the first delivery version of the first embodiment shown in FIG. 1, disposed within the internal carotid artery of a patent, including the distal end of the guide wire and the delivery catheter.

FIG. 5 is a similar view of the first form of the delivery version of the first embodiment seen in FIG. 1, with a different-shaped distal tip of the delivery catheter.

FIG. 6 is a similar view of the distal end of the first form of the delivery version of the first embodiment illustrated in FIG. 4, including a cross-section of the tip of the delivery catheter, a guide wire, and an embolic protection device.

FIG. 7 is a cross-sectional view taken along line 7—7 of FIG. 6.

FIG. 8 is a side elevational partly-broken view of a second delivery version of the first embodiment of the present invention.

FIG. 9 is a similar view of the second delivery version of the first embodiment shown in FIG. 8, including a guide wire, and an embolic protection device at the distal end of the delivery catheter.

FIG. 10 is a side elevational view of a first form of a recovery version of a first embodiment of the present invention, including an inner catheter.

FIG. 11 is a cross-sectional view taken along the line 11—11 of FIG. 10.

FIG. 12 is a side elevational view of the first form of the recovery version of the first embodiment of the present invention, including an outer catheter.

FIG. 13 is a cross-sectional view taken along the line 12—12 of FIG. 11.

FIG. 14 is a side elevational partly-sectional assembly view of the first form of the recovery version of the first embodiment shown in FIGS. 10–13, depicting the outer catheter extending about the inner catheter.

FIG. 17 is a side elevational view of a third form of a recovery version of the first embodiment of the invention, including a guide wire, and an embolic protection device proximate the distal end of the recovery catheter.

FIG. 18 is a similar view of the third form of the recovery version of the first embodiment seen in FIG. 17, with the embolic protection device captured in the expanded tip of the recovery catheter.

FIG. 19 is a side elevational view of a delivery version of a second embodiment of the present invention, including a delivery sheath.

FIG. 20 is a cross-sectional view taken along the line 20—20 of FIG. 19.

FIG. 21 is a side elevational view of a recovery version of the second embodiment of the present invention, including an inner catheter.

FIG. 22 is a cross-sectional view taken along the line 22—22 of FIG. 21.

FIG. 23 is a side elevational view of a recovery version of the second embodiment of the present invention, including an outer catheter.

FIG. 24 is a cross-sectional view taken along the line 24—24 of FIG. 23.

FIG. 25 is a side elevational partly-sectional assembly view of the recovery version of the second embodiment shown in FIGS. 21–24, depicting the outer catheter extending about the inner catheter.

DETAILED DESCRIPTION OF THE PREFERRED EMBODIMENTS

Figure 15:
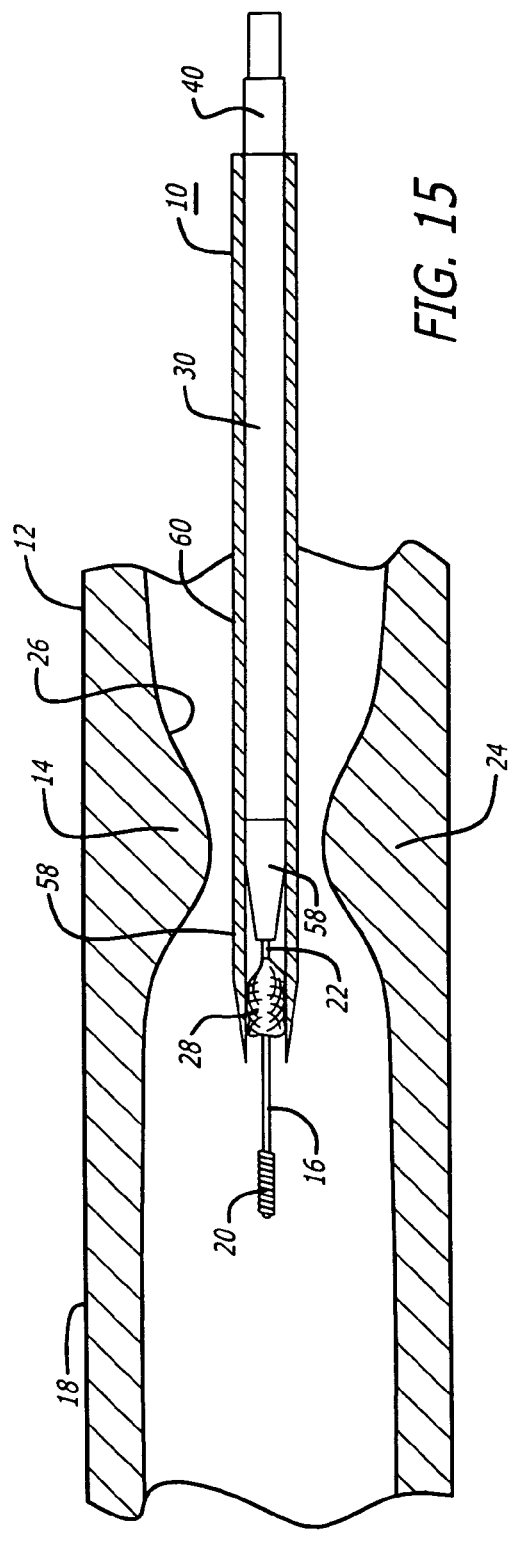
FIG. 15 is a side elevational partly-sectional partly-broken view of the first form of the recovery version of the first embodiment shown in FIG. 14, disposed within the internal carotid artery of a patient, including the guide wire, the inner catheter, the outer catheter, and an embolic protection device.

The present invention is directed to an improved system and method for enabling at least one operator to control the delivery of an embolic protection device to a position in a patient's vasculature distal to an interventional procedure site for deployment of the embolic protection device. It is also adapted to enable the operator to control the removal of the delivery system from the patient's vasculature, in an efficient and effective manner, for the exchange of the delivery and recovery system. It further enables control of the position of a deployed embolic protection device within the patient's vasculature by the operator during an exchange of interventional devices. The system and method are also adapted to enable the at least one operator to control the recovery of the embolic protection device, from the delivered and deployed position thereof, for the exchange of the recovery system.

The present invention is further directed to an improved system and method for enabling the delivery of an embolic protection device to the position in a patient's vasculature distal to the interventional procedure device for the deployment of the embolic protection device, so as to maintain a clinically acceptable profile and flexibility during the delivery and removal thereof through the patient's vasculature. It is further adapted to enable the recovery of the embolic protection device from the position in the patient's vasculature distal to the interventional procedure site, for removal of the embolic protection device, while maintaining the clinically acceptable profile and flexibility during the delivery and removal of the recovery system through the patient's vasculature.

The embodiments of the improved system and method are illustrated and described herein by way of example only and not by way of limitation. While the present invention is described as applied to the carotid arteries of the patient, those skilled in the art will appreciate that it can also be used in other body lumens as well, such as the coronary arteries, renal arteries, saphenous veins and other peripheral arteries. Additionally, the present invention can be utilized when performing any one of a number of interventional procedures, such as stenting, balloon angioplasty, laser angioplasty or atherectomy.

With respect to the drawings, wherein like reference numerals denote like or corresponding parts throughout the drawing figures, and particularly to FIGS. 1–26, in the embodiments of the system and method in accordance with the invention, for example, a system 10 is provided for enabling an interventional procedure to be performed in a blood vessel 12 at an area of treatment 14. The system 10 is adapted to be atraumatic. It includes a guide wire 16 adapted to enable the system 10 to be positioned distal to the area of treatment 14. The system 10 is placed within the carotid artery 18 or other blood vessel of the patient, and is guided into position by the guide wire 16. The guide wire 16 includes a coiled tip 20 at a distal end 22 thereof. The carotid artery 18 has the area of treatment 14 therein, which comprises the interventional procedure site, wherein atherosclerotic plaque 24 has built up against the inside wall 26 which decreases the diameter of the carotid artery 18. As a result, blood flow is diminished through this area.

The therapeutic interventional procedure comprises implanting an expandable interventional instrument at the interventional procedure site 14, to press the build-up of plaque 24 of the stenosis against the inside wall 26, to increase the diameter of the occluded area 14 of the artery 18, and to help restore sufficient flow of blood to the downstream vessels leading to the brain. The expandable interventional instrument not only helps increase the diameter of the occluded area, but helps prevent restenosis in the area of treatment 14. The expandable interventional instrument is adapted to be expanded and deployed at the interventional procedure site 14.

The system 10 of the present invention is adapted to enable the delivery of an embolic protection device 28 to a location distal to the area of treatment 14, and to enable the removal of the embolic protection device 28 from the delivered position thereof. The embolic protection device 28 is adapted to filter the blood in the blood vessel 12, so as to pass blood therethrough and capture embolic material which may be released in the blood vessel 12 during the interventional procedure. The embolic protection device 28 is adapted to be secured to the distal end 22 of the guide wire 16, such that manipulation of the guide wire 16 enables the embolic protection device 28 to be placed within the carotid artery 18 or other blood vessel of the patient and guided into position distal to the area of treatment 14.

Referring to FIGS. 1–18, in a first embodiment of a system pursuant to the present invention, for example, the system 10 is adapted to enable at least one operator to control of the delivery of the embolic protection device 28 to the position in a patient's blood vessel 12 distal to the area of treatment 14, for deployment of the embolic protection device 28. The system 10 is further adapted to enable the at least one operator to control the removal of the delivery system 10, to enable the exchange of the delivery system, and to enable the control of the position of a deployed embolic protection device 28 within the patient's vasculature 12 during an exchange of interventional devices. The system 10 is further adapted to enable the at least one operator to control the removal of the embolic protection device 28 through the patient's vasculature 12, from the delivered and deployed position thereof, for the exchange of the recovery system.

As illustrated in FIGS. 1–9, in a delivery version of the first embodiment of the invention, for example, the system 10 includes the guide wire 16, adapted to be positioned within the blood vessel 12, and to extend to a position distal to the area of treatment 14, and adapted to include the embolic protection device 28 mounted on the distal end 22 thereof. The system 10 also includes a catheter 30, which includes a distal end 32. The catheter 30 has a lumen 34 extending therein to the distal end 32 thereof. The guide wire 16 and the embolic protection device 28 are adapted to extend in and through the lumen 34. The catheter 30 and the guide wire 16 are adapted to enable the embolic protection device 28 to be delivered and deployed distal to the interventional procedure site 14.

The catheter 30 also includes a manipulation-enabling element 36 for enabling the operator to manipulate the guide wire 16 and the catheter 30 independently, so as to enable removal of the guide wire 16 and the catheter 30 through the patient's blood vessel 12. The catheter 30 includes a distal end portion 38, extending from the distal end 32 to a location spaced from the distal end 32, a proximal end 40, and a distal-proximal portion 42, extending from the distal end portion 38 to the proximal end 40. The distal end portion 38 of the catheter 30 is relatively short, for example about twenty centimeters long.

In a first form of the delivery version of the first embodiment of the invention, as depicted in FIGS. 1–7, the distal-proximal portion 42 of the catheter 30 includes a port 44 therein, proximate the distal end portion 42 of the catheter 30, for enabling the guide wire 16 to exit therefrom and extend therethrough and outside and along the relatively longer length of the distal-proximal portion 42 of the catheter 30.

The manipulation-enabling element 36 extends along the distal-proximal portion 42 of the catheter 30. The manipulation-enabling element 40 is adapted to enable the guide wire 16 to be peeled away from and extend outside the catheter 30 and along the distal-proximal portion 42 thereof. The manipulation-enabling element 36 comprises a slit, extending along the distal-proximal portion 42 of the catheter 30. The slit 36 is adapted to enable the catheter 30 and the guide wire 16 to be manipulated by the operator, so as to enable the guide wire 16 to exit from and extend therethrough and outside and along the distal-proximal portion 42 of the catheter 30. After the operator manipulates the guide wire 16 such that the major portion thereof exits the catheter 30 through the port 44, only a minor portion of the guide wire 16 extends in the short length of the distal end portion 38 of the catheter 30, enabling the operator to efficiently manipulate the major portion of the guide wire independent of the catheter 30. Further, with the major portion of the guide wire 16 adapted to exit the catheter 16 for independent manipulation thereof by the operator, less overall length of guide wire 16 is required to enable exchanges thereby.

The catheter 30 further includes a mandrel 48 extending therein, as seen in FIG. 4, adapted to support the catheter 30, to enable the catheter 30 to maintain a clinically acceptable profile and flexibility during delivery and removal thereof through the patient's vasculature 12. The mandrel 48 extends in a second lumen 50 in the catheter 30. The catheter 30 also includes a tip cover 52 at the distal end 34 thereof. The support mandrel 48 may include a flattened distal end 54 thereof, adapted to enable the operator to shape the distal end 52. The shapeable distal end 54 of the support mandrel 48 may be connected to a super elastic distal segment, which is connected to a stainless steel proximal segment. The catheter 30 also includes a handle 56 at the proximal end 40 thereof.

The catheter 30 also includes a tip 58, at the distal end 32 thereof, adapted to be shapeable by the operator, to enable the operator to direct the shapeable tip 58 for movement thereof in the patient's vasculature. The shapeable tip 58 enables the operator to track the system 10 over the guide wire 16 and through tortuous anatomy, without having to rely on the guide wire 16 therefor. The tip 58 is also radiopaque, for enabling the operator to locate the tip 58.

In a second form of the delivery version of the first embodiment of the system 10 pursuant to the present invention, for delivery of an embolic protection device 28, as shown in FIGS. 8–9, the manipulation-enabling element 36 comprises a projection 46, at a location spaced from the proximal end 40 and the distal end 32 of the catheter 30, adapted to communicate with the lumen 34, and to enable a minor portion of the guide wire 16 to extend into the lumen 34 therethrough, and a major portion of the guide wire 16 to extend outside the catheter 30 therefrom. The projection 46 is adapted to enable the catheter 30 and the guide wire 16 to be manipulated independently by the operator. The distal end 32 of the catheter 30 is enlarged for contact with the embolic protection device 28.

As shown in FIGS. 10–18, in a recovery version of the first embodiment pursuant to the present invention, for example, the system 10 includes the guide wire 16, and the catheter 30.

Figure 16:
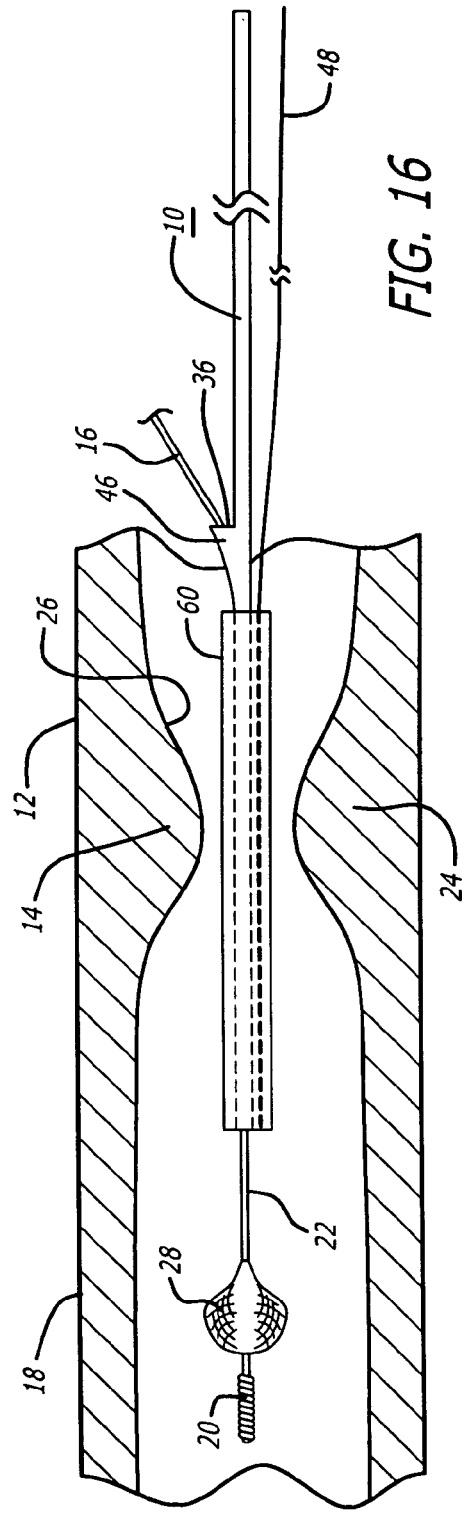
FIG. 16 is a side elevational partly-broken view of a second form of the recovery version of the first embodiment of the present invention, including a guide wire, an inner catheter, an outer catheter, and an embolic protection device, disposed within the internal carotid artery of a patient.
Figure 26:
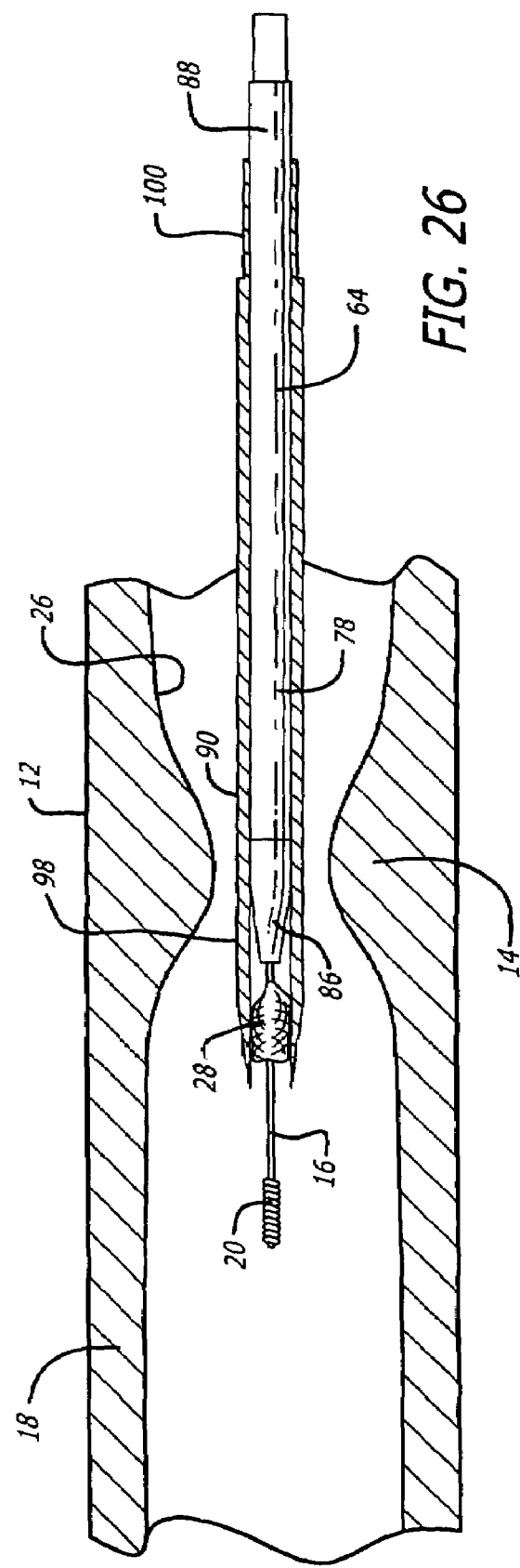
FIG. 26 is a side elevational partly-sectional partly-broken view of the recovery version of the second embodiment shown in FIG. 25, disposed within the internal carotid artery of a patient, including the guide wire, the inner catheter, the outer catheter, and an embolic protection device.

In a first form of the recovery system of the first embodiment in accordance with the invention, as seen in FIGS. 10–15, which corresponds to the first form of the delivery system of the first embodiment as shown in FIGS. 1–7, the catheter 30 comprises an inner catheter, which includes the slit 36, the port 44, the mandrel 48, and the shapeable tip 58. The system 10 further includes an outer catheter 60, adapted to extend about the inner catheter 30, and to be extendable in the distal direction by the operator so as to enclose the embolic protection device 28 for enabling recovery thereof. The outer catheter 60 also includes the slit 36, the port 44, the mandrel 48, and the shapeable tip 58. As seen in FIG. 16, in a second form of the recovery version of the first embodiment, which corresponds to the second form of the delivery version of the first embodiment, as depicted in FIGS. 8–9, the recovery system 10 includes the inner catheter 30, which includes the projection 46, the outer catheter 60, and the mandrel 48. The recovery system 10, in a third form of the recovery version of the first embodiment, as illustrated in FIGS. 17–18, includes the catheter 30, which includes the mandrel 48, and the shapeable tip 58, which is further adapted to be expandable to enable the capture of the embolic protection device 28. The catheter 30 further includes a marker band 62, for enabling the operator to track the location thereof.

Referring to FIGS. 19–26, in a second embodiment of a system pursuant to the invention, for example, a system 64 is provided for enabling the delivery and recovery of an embolic protection device 28 relative to a position in the patient's vasculature 12 distal to an interventional procedure site 14, through the patient's vasculature 12, for deployment of the embolic protection device 28. The system 64 is adapted to maintain a clinically acceptable profile and flexibility during the delivery and removal thereof through the patient's vasculature 12. Elements of the system 64 are comprised of polymer materials such as for example PeBax which is comprised of a thermoplastic polyimide. Also, for the delivery of the embolic protection device 28, the materials are such as to provide substantial flexibility for enabling delivery thereof through the patient's anatomy and for preventing the guide wire 16 from kinking, while providing sufficient rigidity for enabling substantial pushing force to be exerted for delivery and deployment thereof. Further, the dimensions of the elements of the system 64 are such as to provide a low profile for the delivery and recovery thereof and of the embolic protection device 28, while inhibiting vessel trauma.

In a delivery version of the second embodiment of the invention, as depicted in FIGS. 19–20, the system 64 includes a guide wire 16, including a distal end 22, adapted to be positioned within the blood vessel 12 and to extend to the a position distal to the interventional procedure site 14, and adapted to include the embolic protection device 28 mounted on the distal end 22 thereof. The delivery system 64 further includes a delivery sheath 66, including a distal end 68, and has a lumen 70 therein extending in the delivery sheath 66 to the distal end 68 thereof. The guide wire 16 and the embolic protection device 28 are adapted to extend in a through the lumen 70. The delivery sheath 66 and the guide wire 16 are adapted to enable the embolic protection device 28 to be delivered and deployed distal to the interventional procedure site 14. The delivery sheath 66 comprises dimensions and materials adapted to provide a low profile, flexibility for enabling tracking thereof through the patient's vasculature 14, and rigidity for enabling pushing thereon through the patient's vasculature 14, to maintain a clinically acceptable profile and flexibility during the delivery and removal thereof through the patient's vasculature.

The delivery sheath 66 includes a tip 72 at the distal end 68 thereof, adapted to be necked for providing a profile close to the guide wire 16, to inhibit kinking of the guide wire 16 during the delivery and removal of the delivery sheath 66. The delivery sheath 66 also includes a main shaft 74, adapted to provide the low profile, flexibility, and rigidity. The main shaft 74 of the delivery sheath 66 is comprised for example of PeBax, of about 72 Durometer. The tip 72 of the delivery sheath 66 is adapted to be necked, for enabling the embolic protection device 28 to be loaded therein for delivery thereof, and for enabling the release of the embolic protection device 28 for deployment thereof. The tip 72 of the delivery sheath 66 is radiopaque, and is comprised of soft material to prevent vessel trauma. The delivery sheath 66 further includes a proximal end 76, adapted to include a flushing valve including a locking hub.

The delivery sheath 66, in an embodiment thereof, is about 140–145 centimeters in overall length, with a working length of about 25–50 centimeters. The inside diameter of the main shaft 74 is about 0.020 inches, with an outside diameter of about 0.055 inches. The radiopaque necked tip 72 is a soft tip, comprised of a compound including PeBax, of about 40 Durometer, and bismuth, with a clinically acceptable profile and radiopacity, and is about 10–30 centimeters in length, with a maximum outside diameter of about 0.050 inches.

As seen in FIGS. 21–26, in a recovery version of the second embodiment of a system pursuant to the invention, the system 64 is also provided for enabling the recovery of the embolic protection device 28 from the position in the patient's vasculature 12 distal to the interventional procedure site 14, for removal of the embolic protection device 28. The recovery system 64 is adapted to maintain a clinically acceptable profile and flexibility during the delivery and removal thereof through the patient's vasculature 12. The recovery system 64 includes an inner catheter 78, adapted to be positionable adjacent the embolic protection device 28.

The inner catheter 78 includes a distal end 80, a main shaft 82, and a lumen 84 extending in the inner catheter 78 through the main shaft 82 to the distal end 80 thereof. The inner catheter 78 is adapted to extend over the guide wire 16, and the distal end 80 of the inner catheter 78 is adapted to be positionable adjacent the embolic protection device 28. The inner catheter 78 comprises dimensions adapted to enable a smooth transition for movement thereof along the guide wire 16, to inhibit kinking of the guide wire 16 during the delivery and removal of the inner catheter 78, and to maintain a clinically acceptable profile and flexibility during the delivery and removal thereof through the patient's vasculature 12. The inner catheter 78 further includes a tip 86 at the distal end 80 thereof. The main shaft 82 of the inner catheter 78 is comprised for example of PeBax, of about 72 Durometer. The tip 86 of the inner catheter 78 is radiopaque. The inner catheter 78 further includes a proximal end 88, adapted to include a flushing valve including a locking hub.

The inner catheter 78, in an embodiment thereof, is about 145–151 centimeters in overall length, with a working length of about 25–50 centimeters. The inside diameter of the main shaft 82 is about 0.020 inches, with an outer diameter of about 0.055 inches. The radiopaque tip 86 is comprised of a compound including PeBax, of about 40 Durometer, and bismuth.

The system 64, in the recovery version of the second embodiment thereof, further includes an outer catheter 90, including a distal end 92, and a main shaft 94. The outer catheter 90 has a lumen 96 therein extending through the main shaft 94 in the outer catheter 90 to the distal end 92 thereof. The outer catheter 90 is adapted to extend over the inner catheter 78. The outer catheter 90 comprises dimensions and materials adapted to enable a smooth transition for movement thereof along the inner catheter 78, to enable the capturing of the embolic protection device 28, and to inhibit trauma to the patient's vasculature, to maintain a clinically acceptable profile and flexibility during the delivery and removal thereof through the patient's vasculature 12. The outer catheter 90 further includes a tip 98 at the distal end 92 thereof. The main shaft 94 of the outer catheter 90 is comprised for example of high density PE. The tip 98 of the outer catheter 90 is radiopaque. The outer catheter 90 further includes a proximal end 100, adapted to include a flushing valve including a locking hub.

The outer catheter 90, in an embodiment thereof, is about 140–145 centimeters in overall length, with a working length of 25–50 centimeters. The outer catheter 90 is shorter than the inner catheter 78. The inside diameter of the main shaft 94 is about 0.065 inches, with an outer diameter of about 0.075 inches. The radiopaque tip 98 is a soft tip, comprised of a compound including PeBax, of about 40 Durometer, and bismuth.

The outer catheter 90 and the inner catheter 78 of the system 64 interact such that the inner catheter 78 is adapted to enable smooth movement thereof over the guide wire 16, to enable smooth transition from the guide wire 16 to the outer catheter 90, and to resist the development of kinks in the system 64.

Referring to FIGS. 1–18, in a method for the use of the first embodiment of the invention, for enabling the at least one operator to deliver and remove the embolic protection device 28 relative to the position thereof distal to the area of treatment 14 in the patient's blood vessel 12, for example, the system 10 is positioned in and removed from the patient's vasculature 12 by the operator utilizing any one of a number of different methods.

In a method for enabling the operator to delivery the embolic protection device 28 to the position in the patient's vasculature 12 distal to the interventional procedure site 14 for deployment of the embolic protection device 28, as illustrated in FIGS. 1–11, the delivery system 10 is adapted to maintain a clinically acceptable profile and flexibility during the delivery and removal thereof through the patient's vasculature. The guide wire 16 is inserted into the patient's vasculature 12, with the embolic protection device 28 secured thereto and the catheter 30 detachably secured to the embolic protection device 28. The guide wire 16 is then manipulated by the operator to the area of treatment 14, to cross the stenosis in the blood vessel 12, so as to position the embolic protection device 28 for capturing embolic material which may be released in the blood vessel 12 during the interventional procedure. After the embolic protection device 28 is in place, it is deployed by the operator at the position distal to the stenosis in the blood vessel 12. The operator then detaches the catheter 30 from the embolic protection device 28, and manipulates the catheter 30, holding the guide wire 16, so as to remove the catheter 30 from the patient's vasculature 12.

In the first form of the delivery version of the first embodiment as seen in FIGS. 1–7, the operator manipulates the catheter 30 and the guide wire 16 independently for removal of the catheter 30, upon peeling away the guide wire 16 from the catheter 30 through the slit 36 extending along the distal-proximal portion 42 of the catheter 30. The operator, in the second form of the delivery version of the first embodiment as shown in FIGS. 8–9, manipulates the catheter 30 and the guide wire 16 independently for removal of the catheter 30, upon gripping the catheter 30 and the portion of the guide wire 16 extending from the projection 46 in the catheter 30 at the location spaced from the proximal end 40 and the distal end 32 of the catheter 30.

The embolic protection device 28 is recovered by the operator, in the recovery versions of the first embodiment of the invention as illustrated in FIGS. 10–18, for example, after the interventional procedure is performed, by extending a catheter to the embolic protection device 28, capturing the embolic protection device 28, and removing the catheter and the embolic protection device 28 from the patient's vasculature 14.

In a first form of the recovery system 64 as seen in FIGS. 10–15, the operator manipulates the guide wire 16, which extends through the port 44 and through the slit 36, to enable removal thereof. The operator, in the second form of the recovery system 64 shown in FIG. 16, manipulates the portion of the guide wire 16 extending from the projection 46 in the inner catheter 30, along with the inner catheter 30, with the outer catheter 60 extending about the distal end 32 of the inner catheter 30, and with the embolic protection device 28 enclosed in the outer catheter 60. As depicted in FIGS. 17–18, the operator expands the expandable tip 58 of the catheter 30 to capture the embolic protection system 28, and recovers the catheter 30 and the embolic protection system 28.

Referring to FIGS. 19–26 in a method for the use of the second embodiment of the invention, for enabling the delivery and removal of the embolic protection device 28 in relation to the location thereof distal to the occluded area 14 in the patient's vasculature, for example, the system 64 may be positioned in and removed from the patient's vasculature 12 by utilizing any one of a number of different methods.

In a method for enabling the delivery of the embolic protection device 28 to the position in the patient's vasculature 12 distal to the interventional procedure site 14 for deployment of the embolic protection device 28, as seen in FIGS. 19–20, the delivery system 64 is adapted to maintain a clinically acceptable profile and flexibility during the delivery and removal thereof through the patient's vasculature. The guide wire 16 is inserted into the patient's vasculature 12, with the embolic protection device 28 positioned relative to the tip 72 of the delivery sheath 66. The delivery sheath 66 and the embolic protection device 28 are delivered through the patient's vasculature 12 to the area of treatment 14, to cross the stenosis in the blood vessel 12, so as to position the embolic protection device 28 for capturing embolic material which may be released in the blood vessel 12 during the interventional procedure. The delivery sheath 66 is adapted to maintain a clinically acceptable profile and flexibility during the delivery thereof.

After the embolic protection device 28 is in place, it is deployed at the position distal to the stenosis in the blood vessel 12. The delivery sheath 66 is then withdrawn from the embolic protection device 28, and removed through the patient's vasculature 12, while maintaining the clinically acceptable profile and flexibility during the removal thereof.

The embolic protection device 28 is recovered after the interventional procedure is performed, in the recovery version of the second embodiment of the invention as shown in FIGS. 21–26, by inserting the inner catheter 78 into the patient's vasculature 12, through the patient's anatomy, to a position adjacent the embolic protection device 28. During the inserting thereof, the inner catheter 78 is adapted to maintain a clinically acceptable profile and flexibility. The outer catheter 90 is then inserted into the patient's vasculature 12 so as to extend about the inner catheter 78, to a position extending about and capturing the embolic protection device 28 therein. The outer catheter 90 is then removed through the patient's vasculature 12, with the inner catheter 76 and the embolic protection device 28 enclosed therein. A clinically acceptable profile and flexibility is maintained by the outer catheter 90, and the inner catheter 78, during removal thereof from the patient's vasculature 12.

In accordance with the present invention, the particular embodiments set forth above of the system 10 and the system 64 are capable of being positioned in the blood vessel 12. However, other forms of the system 10 and the system 64 may be utilized with the present invention without departing from the spirit and scope of the invention. For example, the system 10 and the system 64 may be comprised of other forms of material. Additionally, while the system 10 and the system 64 are shown as in various shapes in the embodiments herein, they can be formed in any one of a number of different shapes depending upon the construction desired.

Further, the various components may be joined by suitable adhesives such as acrylonitrile based adhesives or cyanoacrylate based adhesives. Heat shrinking or heat bonding may be employed where appropriate. Plastic-to-plastic or plastic-to-metal joints may be effected by a suitable acrylonitrile or cyanoacrylate adhesive. Variations may be made in the composition of the materials to vary properties as needed. Based on the present disclosure, other adhesives and applications may be made known to a person skilled in the art.

In view of the above, the system and method of the first embodiment of the present invention are adapted to substantially enhance the effectiveness of performing interventional procedures, by enabling at least one operator to deliver an embolic protection device to a position for deployment thereof distal to an interventional procedure site in a patient's vasculature, and to remove the delivery system from the patient's vasculature. The article enables the operator to recover the embolic protection device and to remove the system and the embolic protection device from the patient's vasculature. The system and method of the second embodiment of the present invention substantially enhance the effectiveness of performing interventional procedures, by enabling the delivery of an embolic protection device to the position in the patient's vasculature distal to the interventional procedure site, for deployment thereof. The system also enables the delivery and removal of the delivery system from the patient's vasculature, while maintaining a clinically acceptable profile and flexibility. It also enables the recovery of the embolic protection device and the removal of the system and the embolic protection device, while maintaining the clinically acceptable profile and flexibility during the recovery and removal thereof through the patient's vasculature.

While the present invention has been described in connection with the specific embodiments identified herein, it will be apparent to those skilled in the art that many alternatives, modifications and variations are possible in light of the above description. Accordingly, the invention is intended to embrace all such alternatives, modifications and variations as may fall within the spirit and scope of the invention disclosed herein.

What is claimed:

1. A system for enabling at least one operator to control the delivery of an embolic protection device to a position in a patient's vasculature distal to an interventional procedure site for deployment of the embolic protection device, to enable the operator to control the removal of the delivery system from the patient's vasculature for the exchange of the delivery system, and to enable control of the position of a deployed embolic protection device within the patient's vasculature during an exchange of interventional devices, comprising:

a guide wire, including a distal end, adapted to be positioned within the blood vessel and to extend to a position distal to the interventional procedure site, and to include an embolic protection device mounted on the distal end thereof; and a catheter, including a distal end, wherein the catheter has a lumen therein extending in the catheter to the distal end thereof, and wherein the guide wire and the embolic protection device are adapted to extend in and through the lumen, the catheter and the guide wire are adapted to enable the embolic protection device to be delivered and deployed distal to the interventional procedure site, the catheter including a distal portion which forms a housing for maintaining the embolic protection device in a delivery position and a port in communication with the lumen for enabling the guide wire to exit therefrom and extend therethrough outside and along the catheter, and a manipulation-enabling element for enabling at least one operator to manipulate the guide wire and the catheter independently so as to enable removal of the catheter from the patient's vasculature.

2. A system for enabling at least one operator to control the delivery of an embolic protection device to a position in a patient's vasculature distal to an interventional procedure site for deployment of the embolic protection device, to enable the operator to control the removal of the delivery system from the patient's vasculature for the exchange of the delivery system, and to enable control of the position of a deployed embolic protection device within the patient's vasculature during an exchange of interventional devices, comprising:

a guide wire, including a distal end, adapted to be positioned within the blood vessel and to extend to a position distal to the interventional procedure site, and to include an embolic protection device mounted on the distal end thereof; and a catheter, including a distal end, wherein the catheter has a lumen therein extending in the catheter to the distal end thereof, and wherein the guide wire and the embolic protection device are adapted to extend in and through the lumen, the catheter and the guide wire are adapted to enable the embolic protection device to be delivered and deployed distal to the interventional procedure site, and the catheter includes a manipulation-enabling element for enabling at least one operator to manipulate the guide wire and the catheter independently so as to enable removal of the catheter from the patient's vasculature, wherein the catheter further includes a mandrel extending therein, adapted to support the catheter, to enable the catheter to maintain a clinically acceptable profile and flexibility during delivery and removal thereof through the patient's vasculature, the mandrel having a shapeable distal tip which allows the catheter to be steered through the patient's vasculature.

3. A system for enabling at least one operator to control the delivery of an embolic protection device to a position in a patient's vasculature distal to an interventional procedure site for deployment of the embolic protection device, to enable the operator to control the removal of the delivery system from the patient's vasculature for the exchange of the delivery system, and to enable control of the position of a deployed embolic protection device within the patient's vasculature during an exchange of interventional devices, comprising:

a guide wire, including a distal end, adapted to be positioned within the blood vessel and to extend to a position distal to the interventional procedure site, and to include an embolic protection device mounted on the distal end thereof; and a catheter, including a distal end, wherein the catheter has a lumen therein extending in the catheter to the distal end thereof, and wherein the guide wire and the embolic protection device are adapted to extend in and through the lumen, the catheter and the guide wire are adapted to enable the embolic protection device to be delivered and deployed distal to the interventional procedure site, and the catheter includes a manipulation-enabling element for enabling at least one operator to manipulate the guide wire and the catheter independently so as to enable removal of the catheter from the patient's vasculature, wherein the catheter includes a tip, at the distal end thereof, adapted to be shapeable by the operator, to enable the operator to direct the shapeable tip for movement thereof in the patient's vasculature.

4. The system of claim 1, further comprising a recovery system for enabling the at least one operator to control the recovery of the embolic protection device, from the delivered and deployed position thereof, for the exchange of the recovery system.

5. The system of claim 2, wherein the manipulation-enabling element comprises a projection proximate the distal end of the catheter, adapted to communicate with the lumen, and to enable a minor portion of the guide wire to extend in the lumen, and a major portion of the guide wire to extend outside the catheter therethrough.

6. The system of claim 1, wherein the distal end portion extends from the distal end to a location spaced from the distal end, a proximal end, and a distal-proximal portion, extending from the distal end portion to the proximal end, and the manipulation-enabling element extends along the distal-proximal portion of the catheter.

7. The system of claim 4, wherein the recovery system includes the catheter, and the distal end of the catheter includes a tip, adapted to be shapeable by the operator, to enable the operator to direct the shapeable tip for movement thereof in the patient's vasculature, and wherein the shapeable tip is further adapted to be expandable to enable the capture of the embolic protection device.

8. The system of claim 5, wherein the projection is adapted to enable the catheter and the guide wire to be manipulated by the operator.

9. The system of claim 5, wherein the catheter comprises an inner catheter, and the system further comprises an outer catheter, adapted to extend about the inner catheter and to be extendable in the distal direction by the operator so as to enclose the embolic protection device for enabling recovery thereof.

10. The system of claim 6, wherein the manipulation-enabling element is adapted to enable the guide wire to be peeled away from and extend outside the catheter and along the distal-proximal portion thereof.

11. The system of claim 6, wherein the manipulation-enabling element comprises a slit extending along the distal-proximal portion of the catheter.

12. The system of claim 10, wherein the manipulation-enabling element is adapted to enable a minor portion of the guide wire to extend in the lumen, and a major portion of the guide wire to extend outside the catheter therethrough.

13. The system of claim 11, wherein the slit is adapted to enable the catheter and the guide wire to be manipulated by the operator, so as to enable the guide wire to exit from and extend therethrough, and outside and along the distal-proximal portion of the catheter.

14. A delivery system for placing an embolic protection device disposed on a guide wire in a body vessel, comprising:
   an elongate catheter having a distal end and a proximal end, a distal end portion and a distal-proximal portion extending from the distal end portion to the proximal end, the catheter having a lumen extending therethrough which is adapted to receive a guide wire and an embolic protection device disposed on the guide wire, the catheter having a port opening located proximate to the distal end portion of the catheter adapted to enable the guide wire to extend through the distal end portion and exit through the port opening, the distal portion forming a housing for storing the embolic protection device in a collapsed, delivery position.

15. The delivery system of claim 14, wherein the catheter includes a manipulation-enabling element which extends along the length of the distal-proximal portion of the catheter to allow the guide wire to be removed from the portion of the lumen that extends along the distal-proximal portion of the catheter.

16. The delivery system of claim 15, wherein the manipulation-enabling element is adapted to allow the distal-proximal portion of the catheter to be peeled away from the guide wire.

17. The delivery system of claim 16, wherein the manipulation-enabling element is a weakened region in the catheter which extends along the length of the distal-proximal portion.

18. The delivery system of claim 15, wherein the manipulation-enabling element is a slit which extends along the length of the distal-proximal portion.

19. The delivery system of claim 18, wherein the slit extends along the distal-proximal portion and terminates at the port opening.

20. The delivery system of claim 18, further including a handle at the proximal end of the catheter.

21. The delivery system of claim 15, further including a handle at the proximal end of the catheter which includes a lumen for receiving the guide wire and a slot in communication with the lumen for allowing the guide wire to be removed from the handle.

22. The delivery system of claim 14, further including a mandrel extending through the distal-proximal portion of the catheter.

23. The delivery system of claim 22, wherein the mandrel has a shapeable distal end which can be bent into a desired shape to allow the catheter to be steered through tortuous anatomy independent from the guide wire.

24. The delivery system of claim 14, wherein the distal end of the catheter includes a shapeable member which can be bent into a particular shape to allow the catheter to be steered through tortuous anatomy.

25. The delivery system of claim 24, further including a mandrel extending through the distal-proximal portion of the catheter.

* * * * *

UNITED STATES PATENT AND TRADEMARK OFFICE
CERTIFICATE OF CORRECTION

PATENT NO. : 6,929,652 B1
DATED : August 16, 2005
INVENTOR(S) : Christopher C. Andrews et al.

It is certified that error appears in the above-identified patent and that said Letters Patent is hereby corrected as shown below:

Column 6,
Line 47, delete "proximate" and insert -- proximal to --.

Column 8,
Line 36, delete "control of" and insert -- control --.

Column 9,
Line 11, delete "proximate" and insert -- proximal to --.

Column 10,
Line 61, delete "the a position" and insert -- a position --.
Line 67, delete "in a".

Column 12,
Line 49, delete "delivery" and insert -- deliver --.

Signed and Sealed this

Third Day of January, 2006

JON W. DUDAS
*Director of the United States Patent and Trademark Office*